United States Patent [19]

Kim et al.

[11] Patent Number: 5,081,110
[45] Date of Patent: Jan. 14, 1992

[54] METHOD OF KILLING SARCOMA CELLS USING FLUDARABINE PHOSPHATE AND IONIZING RADIATION

[75] Inventors: Jae H. Kim, Tenafly, N.J.; Alan A. Alfieri, Garden City, N.Y.; Sang H. Kim, Flushing, N.Y.; Zvi Fuks, New York, N.Y.

[73] Assignee: Sloan-Kettering Institute For Cancer Research, New York, N.Y.

[21] Appl. No.: 283,734

[22] Filed: Dec. 13, 1988

Related U.S. Application Data

[63] Continuation-in-part of Ser. No. 844,864, Mar. 27, 1986, abandoned.

[51] Int. Cl.$^5$ .................... A61K 31/70; A61W 5/00
[52] U.S. Cl. .......................................... 514/47; 600/1
[58] Field of Search .............................. 514/47; 600/1

[56] References Cited

PUBLICATIONS

Chemical Abstracts 98:209564e (1983).
Chemical Abstracts 99:187044b (1983).
Spencer et al, Cancer Research Supplement, Part 2, vol. 25, No. 4, May 1965, p. 850 (3018).
Moossa et al., Comprehensive Textbook of Oncology (2/4/86), Williams & Wilkins, Balto., Md., pp. 257–268.

*Primary Examiner*—Jerome D. Goldberg
*Attorney, Agent, or Firm*—John P. White

[57] ABSTRACT

This invention provides a method of killing sarcoma cells in a patient by administering to the patient an effective amount of fludarabine phosphate effective to inhibit the repair of potentially lethal damage to the sarcoma cells and exposing the patient to an effective amount of ionizing radiation, effective to kill the sarcoma tumor cells in the patient.

7 Claims, 3 Drawing Sheets

METHOD OF KILLING SARCOMA CELLS USING FLUDARABINE PHOSPHATE AND IONIZING RADIATION

This application is a continuation-in-part of U.S. Ser. No. 844,864, filed Mar. 27, 1986, now abandoned the contents of which are hereby incorporated by reference.

The invention described herein was made in the course of work under grant No. CA-34648 from the National Cancer Institute, U.S. Department of Health and Human Services. The U.S. Government has certain rights in this invention.

BACKGROUND OF THE INVENTION

Throughout this application, various publications are referenced and citations provided for them. Some of the references are referred to by arabic numerals within parenthesis. Full bibliographic citations for these references are provided in the specification immediately preceding the claims. The disclosure of these publications in their entireties are hereby incorporated by reference into this application to more fully describe the state of the art to which this invention pertains.

Much of the disclosure of U.S. application Ser. No. 844,864, filed Mar. 27, 1986 has been published. See, e.g., Kim et al., Cancer Letters, vol. 31, pp. 69–76, 1986.

Exposure of mammalian cells to ionizing radiation results in the production of potentially lethal damage (PLD), the repair of which depends on the proper post-irradiation condition under which cells are held. See, e.g., Phillips et al, Radiat. Res. 29: 414 (1966); Hahn et al, Curr. Top Radiat. Res. Q. 8 39 (1972). The post-irradiation exposure of irradiated cells to restrictive conditions where they cannot enter the first semi-conservative DNA replication after irradiation results in enhanced radiation induced cell killing, as has been shown by Iliakis, et al., Int. J. Radiat. Biol. 42:417 (1982). Such conditions are frequently found in the microenvironment of large solid tumors, which are usually characterized by low pH, low oxygen tension and a nutritionally deficient state. The possible importance of PLD repair in tumor control by radiation has recently received attention following cell culture studies that have demonstrated a correlation between radiocurability of human tumors and their capacity for PLD repair in vitro. Weichselbaum, et al., Radiation Biology in Cancer Research, p. 345 et. seq. (Raven Press, 1980); Weichselbaum et al, Brit. J. Cancer 46: 532 (1982)..

The classes of agents reported to inhibit the repair of PLD in cell culture systems are inhibitors of DNA synthesis and of energy metabolism. Iliakis, Radiat. Res, 82: 537 (1980); Nakatsugawa et al, Int. J. Radiat. Biol., 41: 343 (1982); Hahn, et al, Brit. J. Cancer 50:657 (1984). Among the inhibitors of DNA synthesis, β-arabinofuranosyl adenine (β-ara-A), an anti-viral agent, was shown to be a potent inhibitor of PLD repair. However, when β-ara-A was tested for its radiation potentiating effects on an in vivo murine tumor, the study failed to show any potentiation of radiation effects. Nakatsugawa, Modification of Radiosensitivity in Cancer Treatment, p.221 (Acad. Press, 1984). The reason for the negative result of β-ara-A may be related to the fact that β-ara-A is readily inactivated by hydrolysis to arabinofuranosyl hypoxanthine via adenosine deaminase. An alternative approach to potentiating the antiviral and anti-neoplastic activity of β-ara-A is to use an analog which is not inactivated by adenosine deaminase. 2-fluoro-arabinofuranosyl adenosine monophosphate (fludarabine phosphate) the first phosphorylated metabolite of 2-fluoro-ara-A, has been shown to inhibit DNA polymerase and ribonucleotide reductase in vitro. Brockman et al, Biochem. Pharmacol. 26:2193 (1977); White et al, Proc. Am. Assoc. Cancer Res., 27:33 (1981).

Fludarabine phosphate is a synthetic analog of β-arabinofuranosyl adenine, which has been found not to be inactivated by adenosine deaminase, unlike β-ara-A.. In view of the fact the β-ara-A was useful as a PLD inhibitor in vitro, but in vivo tests proved negative, fludarabine phosphate was used as a potential inhibitor of potentially lethal damage in radiotherapy in vivo. The results obtained, using this compound, show that fludarabine phosphate is a useful therapeutic agent in radiotherapy.

SUMMARY OF THE INVENTION

This invention provides a method of killing sarcoma cells in a patient by administering to the patient an effective amount of fludarabine phosphate effective to inhibit the repair of potentially lethal damage to the sarcoma cells and exposing the patient to an effective amount of ionizing radiation, effective to kill the sarcoma tumor cells in the patient.

DETAILED DESCRIPTION OF THE INVENTION

This invention provides a method of killing sarcoma cells in a patient by administering to the patient an effective amount of fludarabine phosphate effective to inhibit the repair of potentially lethal damage to the sarcoma cells and exposing the patient to an effective amount of ionizing radiation, effective to kill the sarcoma tumor cells in the patient.

In one embodiment of this invention, the amount of fludarabine phosphate effective to inhibit the repair of potentially lethal damage to the tumor cells comprises from about 25 to about 375 mg/m$^2$, particularly from about 50 to about 375 mg/m$^2$, and more particularly from about 75 to about 200 mg/m$^2$.

In one embodiment, the amount of ionizing radiation effective to kill the tumor cells comprises from about 6 to about 10 Gray units. In another embodiment, the effective amount of ionizing radiation is about 8 Gray units.

This invention also provides a method of killing sarcoma cells in a patient as disclosed hereinabove, wherein at least one hour prior to exposing the patient to ionizing radiation, the patient is administered an effective amount of fludarabine phosphate.

As will be apparent to one skilled in the art, the actual amount of fludarabine phosphate which should be employed will vary, depending upon the subject or patient's age, weight, general health, and so forth. Additionally, the method of employing the compounds and compositions will depend upon such characteristics. Subcutaneous injection, intravenous injection, oral administration, and so forth, are various means of administration which can be used. The means and form of administration (e.g, liquid, solid, lotion, pill, and so forth) will again vary, depending upon the size and location of the tumor being treated, as well as the other factors set forth supra.

This invention is further illustrated in the Experimental Details and Experimental Discussion sections which follow. These sections are set forth to aid in an understanding of the invention but are not intended to, and should not be construed to, limit in any way the invention as set forth in the claims which follow thereafter.

EXPERIMENTAL DETAILS

Materials and Methods

First Series of Experiments

Figure 1:
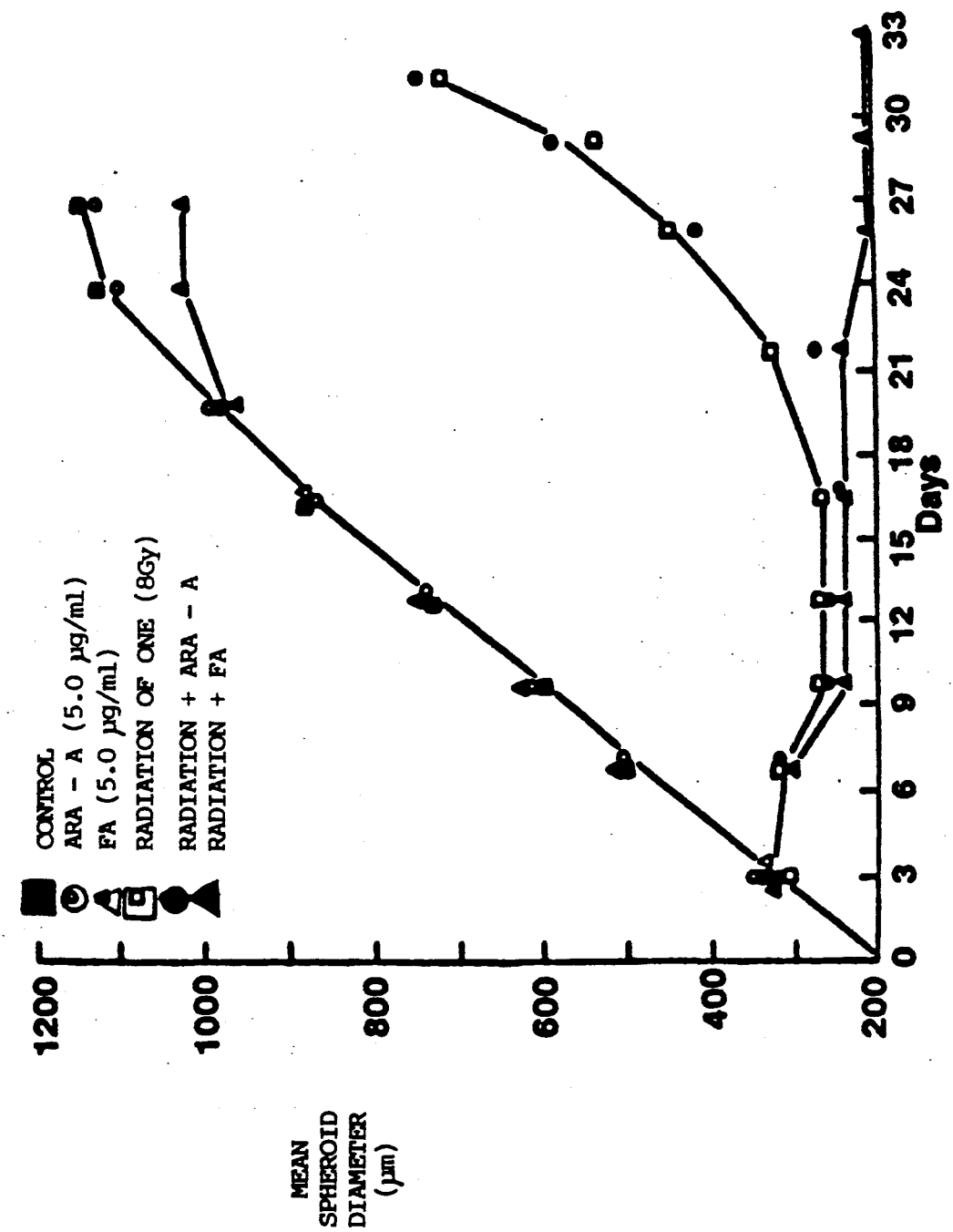
FIG. 1 shows the decrease in spheroid diameter of tumors, as treated with fludarabine phosphate and control models, over time.

For in vitro tumor studies, S-3 multicellular tumor spheroid systems (MTS) was used. The method for producing MTS was essentially the same as that described by Yuhas et al, Cancer Res., 37:3639 (1977). When MTS were exposed to $\beta$-ara-A or fludarabine phosphate (5 $\mu$g/ml), there was barely detectable growth delay in comparison to untreated control MTS. To assess the combined effect of radiation and drugs, MTS were irradiated with a single dose of 8 Gy, and were incubated in the presence of drugs for up to 30 days. The results plotted in FIG. 1 show a significant enhancement of radiation effect by fludarabine phosphate, but not by $\beta$-ara-A.

Because of the striking enhancement of radiation effects on the MTS growth by fludarabine phosphate, in vivo experiments were performed to determine whether fludarabine phosphate possesses the radiosensitizing effects on in vivo tumors. For in vivo tumor studies, the methylcholanthrene induced fibrosarcoma (Meth-A) grown in isogenic BALB/c (H-2$^d$) male mice was used. The tumor doubling time was about 1.5 days in exponential growth. Details of tumor maintenance and inoculation procedures have been described by Kim et al., Oncoloqv 41:36 (1984). For the combined studies, cells were inoculated intramuscularly into the distal thigh region. At the time of irradiation, the average tumor volume was about 650 mm$^3$.

Figure 2:
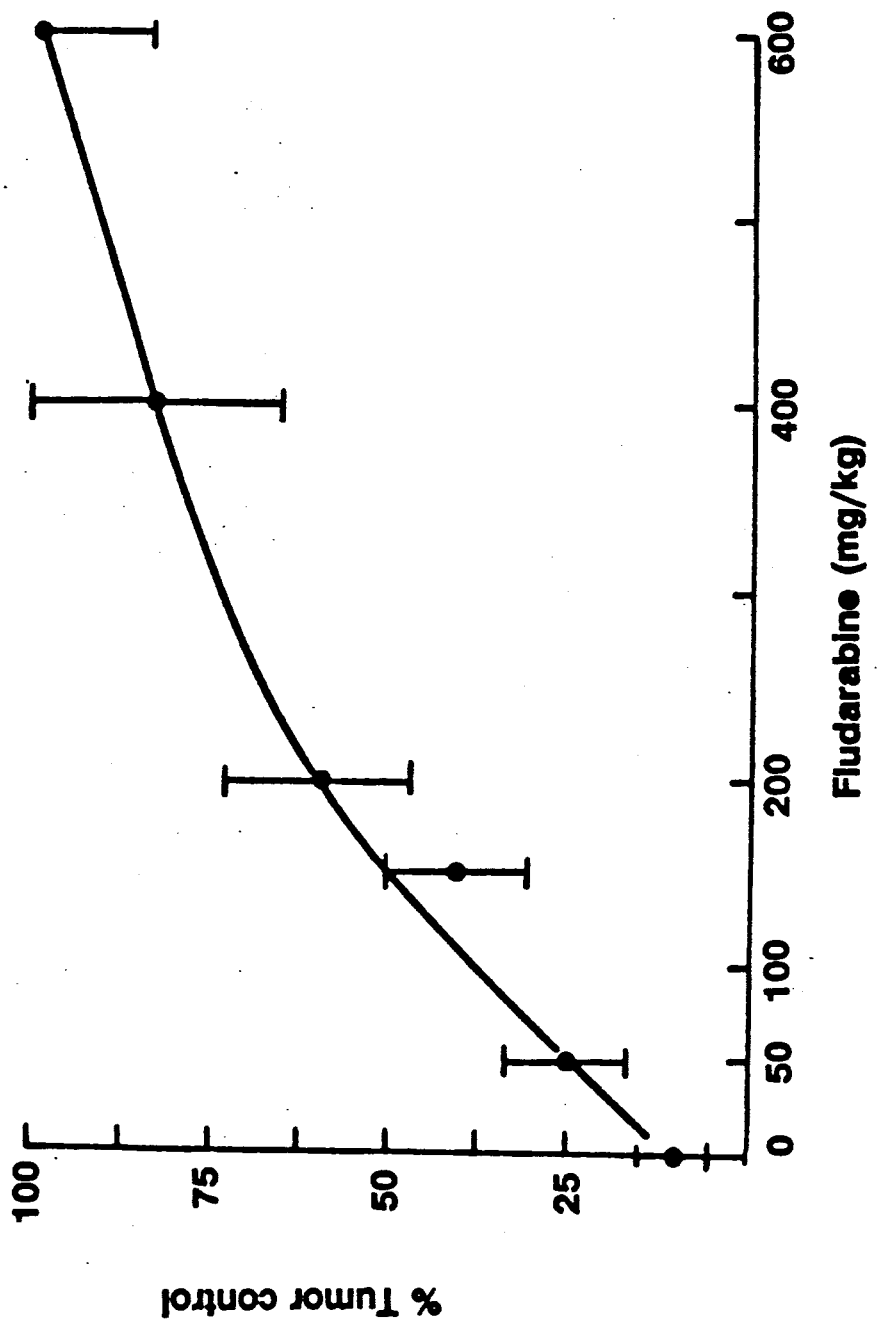
FIG. 2 shows the relationship between tumor control and the dosage of fludarabine phosphate administered using the radiation treatment.
Figure 3:
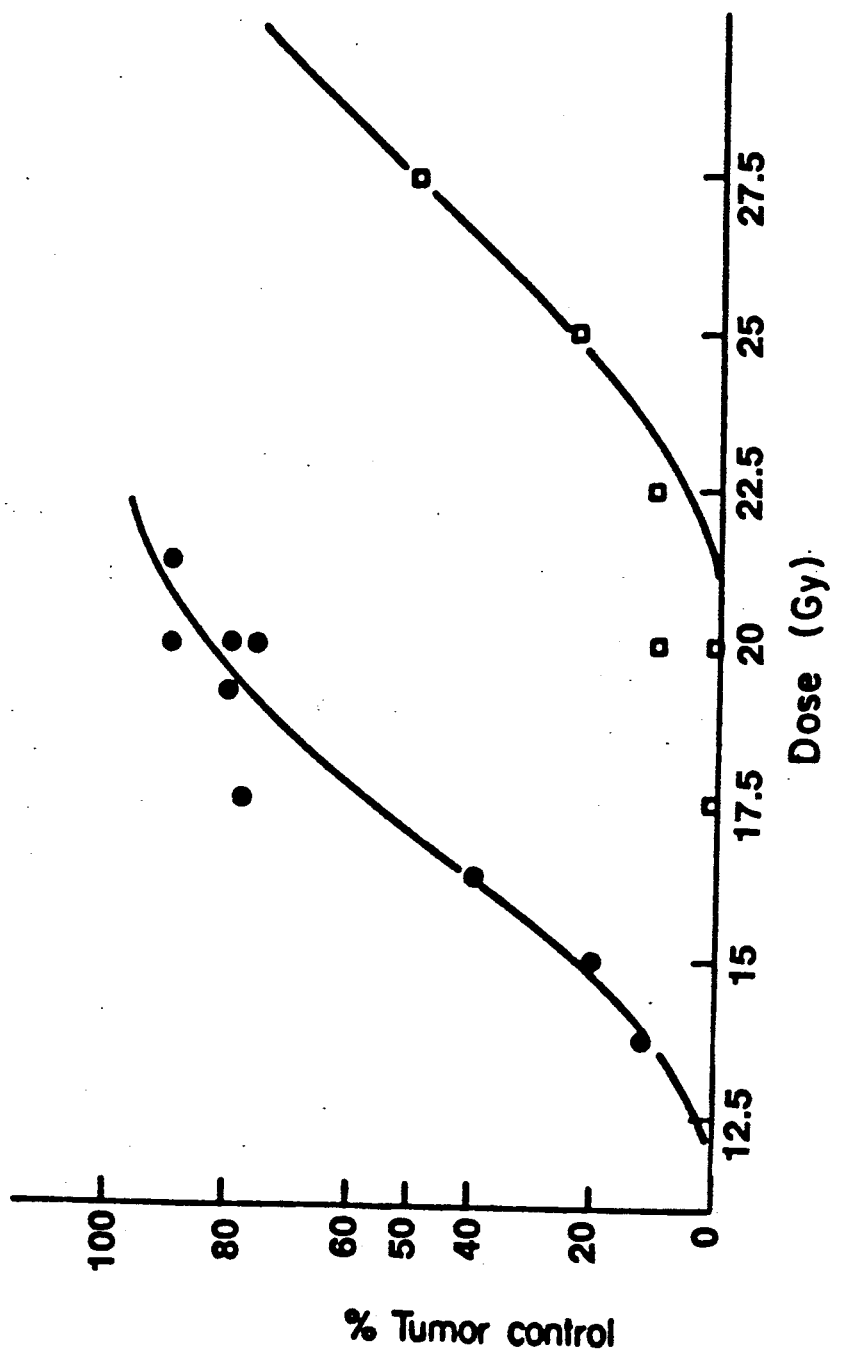
FIG. 3 shows the determination of tumor control dose of Meth-A. at a particular dosage of fludarabine phosphate, using single doses of radiation.

Prior to the determination of dose modification, experiments were performed to determine the importance of the sequence and time of fludarabine phosphate administration with respect to x-irradiation and drug concentration. The maximum sensitizing effect of the drug was obtained at 1 hr prior to x-irradiation. FIG. 2 shows the rate of tumor control vs drug concentration after a single dose of 20 Gy. A single dose of 20 Gy alone resulted in less than 10% S$^{-3}$ tumor control. The tumor control rate in the presence of drug, however, steadily increased to a maximum (100%) at a drug concentration of 600 mg/kg. Further studies were carried out on combined drug and single x-irradiation to determine the dose modification factor (DMF) of fludarabine phosphate. The tumor control dose of 50% (TCD$_{50}$) for Meth-A at 400 mg/kg of fludarabine phosphate when compared to single dose radiation was 17.5 Gy and 27.5 Gy, which correlates to a DMF of 1.6 (FIG. 3).

The magnitude of the sensitizing effects of radiation by fludarabine phosphate is quite impressive (FIG. 2.). More than 90%A tumor cure can be obtained with a single injection of fludarabine phosphate (600 mg/kg) after a single dose of radiation (20 Gy). The LD 10 of acute fludarabine phosphate in BALB/c mice is >1.6 g/kg. The administration of fludarabine phosphate by itself at concentration 600 mg/kg did not induce any detectable inhibitory effects on tumor growth. An important observation with regard to fludarabine phosphate treatment is its effects on normal tissues. There was no enhanced skin reaction observed in the combined treatments when compared to the radiation alone groups at equivalent doses.

Although the molecular mechanism of PLD repair process have not been well understood, the repair synthesis of DNA has been implicated as a major biochemical target. Nakatsugawa, supra; Iliakis, supra. Hence, several chemicals that possess the capacity of DNA polymerases inhibition may also be potential candidates for a new class of radiosensitizers. Several anti-viral agents, including $\beta$-ara-A and fludarabine phosphate, are well known to inhibit DNA polymerase. Indeed, preliminary indications suggest that the new anti-viral drug FMAU (fluoromethyl-arabinofuranosyl uracil) appears to be an excellent PLD repair inhibitor in MTS system. Fox et al, Med. Chem. Advances, (p. 27), (Pergamom Press, 981); Kim et al, 33rd Ann. Meetinq Radiat. Res. Soc., (pp. 78), (1985).

Second Series of Experiments

The 9L gliosarcoma cell line used in these studies and has been described previously by Dr. K. Wheeler, Methods In Tumor Biology: Tissue culture and animal tumor models. The cells have been maintained as exponential cultures in Eagle's minimun essential medium with 10% fetal calf serum and supplemented with an additional 1% vitamin and 1% non-essential amino acid mixture. Prior to implantation, cells were trypsinized and resuspended in Hanks' balanced salt solution for cell counting on the model ZM Coulter counter. A final dilution of 10/6 cells per milliliter was made in the presence of Eagle's medium. Intracraneal implants were performed on Fischer 344 male rats (Charles River Breeding Laboratories, Wilmington Mass. weighing approximately 185 to 225 grams that were anesthetized intraperitoneal with 50 mg/Kg sodium pentobarbital (Nembutal) Rats were positioned in a stereotactic head holder and the scalp opened with a midline incision of approximately 2 cms exposing the frontal and temporalis bones to accomodate tumor implantation. A 0.5 mm hole was drilled through the skull without breaking the dura, with a No 6 dental drill bit. The intracraneal injection site was 2.5 mm anterior and 2.0 to the right of the bregma at a depth of 3.0 cm into the brain parenchyma. A Hamilton syringe with a sleeve attached to a 23 gauge needle served as a stop allowing the needle to protrude only 3.0 mm into the prontoparietal cortex of the brain. Cell suspensions were constantly agitated by a magnetic spin bar during the implantation procedure and 10/4 9L cells were inoculated intracerebrally in 10 $\mu$l injection. The area of implantation was covered with physiological saline before needle insertion to maintain hydrostatic pressure upon needle removal. Hydrogen peroxide was immediately applied to sterilize the area and lyse any residual cells followed by sterile bone wax to seal the hole. Approximately 24 hours after intracerebral injection, animals were inoculated subcutaneously with 1.0 mg of dexametasone. 9L gliosarcoma cells can be propagated in intracerebral inoculation into rats and quantitative clonogenic assays are feasible using standard in vitro colony assays. As with the human malignant gliomas, 9L gliosarcoma has been shown to have relatively radioresistant sensitivity (Do:195 cGy; n:4–6). The detailed studies by Wheeler et al. have failed to demostrate any evidence of a hypoxic fraction in these solid tumors growing at either intracerebral or subcutaneous sites.

Radiation treatment was done with a Philips MGC 30 hybrid ortovoltage unit at 320 KVP, 10 mA, 0.5 mm Cu filter (HVL for 1.78 mm Cu). Dose rate in air: 157 Ro/minute, in tissue 149 rads/minute at 50 cms.

Rats were lightly anestethized with 30 mg/kg sodium pentobarbital (Nembutal, H. Schein, Inc.), placed in a stereotactic head holder and a specially designed shield was used in order to protect normal structures.

Total radiation dose, as defined, was delivered as a single dose in parallel opposed fields, the 6th day after inoculation, when histological epithelial proliferation is confirmed. All doses were defined at midline, at 4.0 mm from the frontoparietal cortex of the brain and at 2.5 mm anterior from the bregma, approximate site and extension of the tumor at Day 6 after inoculation.

Animals were observed daily until death by primary disease or were followed for long term survival at 120 days. All dead or dying animals were formalin fixed for histopathological examination with hematoxylin eosin stain for tumor and luxols fast blue stain for myelin changes.

Fludarabine Phosphate, (9-B-D-Arabinosyl-2-fluoroadenine-5'-phosphate) or F-Ara-AMP, the synthetic analog of B-Ara-A was obtained from the Division of Cancer Treatment of National Cancer Institute. Betheseda Maryland, and given into the peritoneal cavity of the rat at 400 mg/kg as 100 mg/ml one hour before radiation treatment.

Results

20 & 25 Gy alone acute dose, results in no cure and/or significant delay in survival. The combination of 20 and 25 Gys and F-Ara-FMP, as described, results in an increase of cures and an increase of life span of the remaining local failures compared to the brain tumor radiation alone control groups.

Discussion

Glioblastoma is resistant to therapeutic radiations and its benefit is basically paliative, increase of life span and its cuality.

Several factors could be contributing to the radioresistance of this human brain malignant tumor. In an attempt to somehow modify this condition, F-Ara-AMP was used, the long serum lasting soluble version of B-Ara A, known to potenciate both the in vitro and in vivo radiation effect, by virtue of inhibiting the repair of the radiation damaged malignant cells that are in a potential lethal condition. In this study positive results could be obtained in the 9L rat brain tumor model.

No attempt was made to optimize time interval prior radiation treatment, nor concentration/dose dependency of the drug, which was done following previous work on the other tumor model. The radiation dose dependency of the combined treatment could give a guide for reducing total radiation dose if complete or maximal plateau responses are achieved in order to avoid or reduce side effects.

Third Series of Experiments

Ara-A (9-beta-D-arabinofuranosyladenine) is one of several adenosine analogs with antiviral and anti-neoplastic properties (1,2). Ara-A is inactivated by hydrolysis to Ara-H (9-beta-D-arabinofuranosylhypoxanthine) via adenosine deaminase (2). Inhibition of this enzyme with 2'-deoxycoformycin enhances the antitumor activity of Ara-A (3,4). An alternative approach to potentiating the anti-tumor activity of Ara-A is to use an analog which is not inactivated by adenosine deaminase. The observation that 2-fluoroadenosine is not a substrate for this enzyme suggested that 2-fluoro-ara-A might be active as an antitumor agent (5). In in vitro studies, 2-fluoro-ara-ATP inhibited DNA polymerase and ribonucleotide reductase (6).

2-Fluoro-ara-A is poorly soluble in water and is therefore difficult to administer. 2-Fluoro-ara-AMP (fludarabine phosphate), its mono-phosphorylated metabolite, is water soluble (5,7). In the L1210 murine leukemia system, fludarabine phosphate possesses antineoplastic activity similar to that of the combination of Ara-AMP plus 2'-deoxycoformycin; Ara-AMP alone is less effective(5). Fludarabine phosphate is also active in the LX-1 human lung tumor and P388 leukemia. In schedule-dependency testing against murine leukemia, fludarabine demonstrated optimal activity when given daily for 5 days (8).

The aim of this study is to determine whether the use of combined flurarabine phosphate and radiation thereapy enhances the tumor control rate of radioresistant superficial cancers.

Preclinical Toxicoloqy

Toxicologic evaluation identified the LD10 in mice as 1118 mg/sq m/day. Mice demonstrated decreased activity, dehydration, and myelosuppression. No toxic signs were noted in dogs at 1/10 this dose, 112 mg/sq m/day. At higher doses, toxic signs included anorexia, dehydration, emesis, diarrhea, myelosuppression, hepatic dysfunction and renal injury (8).

Clinical Studies

The acute dose-limiting toxic effect of fludarabine phosphate is myelosuppression. The recommended Phase II dosage in solid tumor patients varied only slightly with differing schedules, i.e., 125 mg/m² single dose every 21 days, or 18 to 25 mg/m²/day $\times$ 5 days at 21 to 28 day intervals by i.v. injection, or 25 mg/m²/day $\times$ 5 days by continuous infusion (9–11).

In Phase II studies in patients with sarcomas, employing a dosage range/course of 90 to 150 mg/m², fludarabine has produced objective tumor regression in patients with lymphoproliferative disorders and clinical improvement in chronic lymphocytic leukemia. It has been inactive in patients with lung or colorectal cancers (11).

Higher dosages of fludarabine phosphate have been studied in patients with acute leukemia. Drug dosages 480mg/m²/course have produced complete remission in a study at Memorial Sloan-Kettering Cancer Center. Unfortunately, these dosages have also produced unacceptable neurologic symptoms with cortical blindness, coma and death (12,13). Serious neurologic symptoms occurred in 13 of 47 patients treated at these high dosages. In contrast CNS toxicity has been observed in only one of 443 patients with the solid tumor dosage schedules for an incidence of 0.2% (13). The affected patient received a cumulative dose of 300 mg/m² over 3 courses; a causal relation between administration of fludarabine and the CNS symptoms is considered "probable". The CNS toxic effect appears dose-rate related; some solid tumor patients have received over 10 courses without CNS toxicity.

Pharmaceutical Information

Fludarabine phosphate is supplied by the Division of Cancer Treatment, National Cancer Institutes of Health, Bethesda, MD, as a white lypophilized powder in 200 mg vials with sodium hydroxide to adjust the pH. Reconstitution with 2 ml of sterile water for injection USP results in a drug concentration of 100 mg/ml at pH 7.0 to 8.5.

The intact vials should be stored at 2°–8° C.

Shelf life surveillance studies of the intact vial are ongoing. Fludarabine phosphate is relatively stable in aqueous solution. Over a pH range of approximately 4.5 to 9.0 in aqueous buffer solution stored at 65° —C., less than 4% decomposition occurred in one day and less than 10% occurred in 4 days. From this pH profile, the optimum pH was determined to be approximately 7.6. At a concentration of 25 mg/ml in distilled water stored at room temperature in normal laboratory light, fludarabine phosphate exhibited less than 2% decomposition in 16 days. Diluted to a concentration of 1 mg/ml in 5% dextrose USP or in 0.9% sodium chloride Injection USP, less than 3% decomposition occurred in 16 days at room temperature under normal laboratory light (8).

The single-use lyophilized dosage form contains no antibacterial preservatives.

Exposure of mammalian cells to ionizing radiation results in the production of potentially lethal damage (PLD), the repair of which is dependent upon the post-irradiation conditions under which cells are held. Even relatively brief exposure of irradiated cells to restrictive growth conditions; which prevents the cells from entering semi-conservative DNA replication after irradiation, results in reduced radiation-induced cell killing (16,17). Such conditions are frequently found in the microenvironment of large sarcomas, which is usually characterized by low pH, low oxygen tension and a nutritionally deficient state. This decrease in radiation-induced cell kill in ascribed to repair of PLD. The possible importance of PLD repair in clinical resistance to irradiation has recently received support from cell culture studies that have demonstrated a positive correlation between radioresistance of human tumors and their capacity for PLD repair in vitro (18,19).

At least two classes of agents inhibit the repair of PLD in cell culture systems; i.e., inhibitors of DNA synthesis, and drugs which perturb energy metabolism (20,23). Among the inhibitors of DNA systhesis, (arabinosyladenine )(Ara-A), an antiviral agent, was shown to be a potent inhibitor of PLD repair in vitro. However, when Ara-A was tested for its radiation potentiating effects on an in vivo murine tumor, the sutdy failed to show any potentiation of radiation effects (17). The reason for the negative result of Ara-A may be related to the fact that the drug is readily inactivated by hydrolysis to arabinofuranosyl hypoxanthine via adenosine deaminase.

An alternative approach to potentiating the anti-viral and anti-neoplastic activities of Ara-A is to use an analog which is not inactivated by adenosine deaminase. 2-fluoroarabinofuranosuyl adenine monophosphate (fludarabine phosphate), the mono-phosphorylated metabolite of 2-fluoroara-A, has been shown to inhibit DNA polymerase and ribonucleotide reductase in vitro (5). Since fludarabine phosphate is not readily inactivated by adenosine deaminase and is currently undergoing Phase II clinical trials for anti-tumor and anti-viral activities in humans, its radiosensitizing effects on in vitro and in vivo .tumors was investigated.

Exposure of HeLa S-3 multi-cellular tumor spheroids (MTS) to Ara-A or fludarabine phosphate immediately before X-irradiation produced a significant potentiation of radiation effects on MTS growth by fludarabine phosphate but not by Ara-A. The combined treatment of single dose of x-irradiation and fludarabine phosphate on Meth-A fibrosarcomas in BALB/c mice produced more than 90% tumor control, while radiation alone resulted in less than 10% control. There was no increase in skin reaction following the combined treatments (24).

Discussion

The strength of radiation therapy is in the control of local tumor masses; nevertheless, local control is not always achieveable. The control of locally bulky disease will assume its most important role when the treatment of (less bulky) disseminated disease is effective through chemotherapy and as cancers are more frequently detected while still localized. Particularly in this setting, combined treatment with a radiosensitizer and radiotherapy can have a major impact on the total care of the cancer patient through improved local control of tumors.

The primary objective of this proposal is to establish whether, and to what degree, fludarabine phosphate increases the effect of radiation on multiple superficial lesions from melanomas, soft tissue sarcomas and breast cancer.

If the postulated biological advantage of this inhibitor of radiation-induced potentially lethal damage repair (PLDR) of radiation is demonstrated, in superficial tumors, it will provide quantitative information of great value in designing the optimum time dose fractionation schedules for combined treatments of deep-seated tumors.

The study would also provide a clinical model for testing of other PLDR inhibitors that exhibit excellent radiobiological properties in preclinical systems.

In accordance with an aspect of this invention, the following treatment plan, drug dose, and radiation therapy may be implemented.

Treatment Plan: The plan is to treat superficial (cutanteous subcutaneous) cancerous lesions that require palliative radiation (RT). One lesion is to be treated with RT one day before fludarabine phosphate (F) and the other lesion to be treated with RT given within one hour after drug administration (RT+F).

Drug Dose: A single dose of fludarabine phosphate, 125 mg/m$^2$, will be administered one hour prior to radiation therapy. The drug will be administered in 100 c.c of 5% dextrose solution intravenously over 20 minutes.

Radiation Therapy: A single dose of 8 Gy will be delivered to the area containing lesions with a margin of at least 2 cm. around the tumor volume. If lesions are less than 4 cm. in depth, electron beams of chosen energy will be employed. Tumors extending into more than 4 cm. in depth will be irradiated with megavoltage photon beams with an appropriate bolus on the surface of the lesion.

References

1. Schabel FM, Jr. The antiviral activity of 9-beta-D-arabinofuranosyladenine (Ara-A). Chemotherapy 13:321–388, 1968.
2. Brink, J. J. and LePage G. A. Metabolic effects of 9-D-arabinosylpurines in ascites tumor cells. Cancer Res. 24:312-318, 1964.
3. LePage G. A. Worth L. S., and Kimball AP. Enhancement of the antitumor activity of arabinofuranosyladenine by 2'-deoxycoformycin. Cancer Res 36:1481-1485, 1976.

4. Cass, C. E. and Au-Yeung, T. H. Enhancement of 9-beta-D-arabinofuranosyladenine cytoxicity to mouse leukemia L1210 in vitro by 2'-deoxycoformycin. Cancer Res. 36:1486–1491, 1976.
5. Brockman R. W., Schabel, F. M., Jr., and Montgomery J. A. Biologic activity of 9-beta-D-arabinofuranosyl-2-fluoradenine. a metabolically stable analog of 9-beta-D-arabinofuranosyladenine. Biochem. Pharmacol. 26:2193–2196, 1977.
6. White, L., Shaddix, S. C. Chen, Y. C. et al. Inhibition of ribonucleotide reductase and DNA polymerases of tumor cells by 9-beta-D-arabinosyl-2-fluoradenine 5-triphosphate (2-F-ara-ATP). Proc. Am. Assoc. Cancer Res. 22:23, 1981.
7. LePage, G. A., Lin, Y. T., Orth, R. E. and Gottlieb, J. A. 5,-nucleoside analogs in man. Cancer Res. 32:2441–2444, 1972.
8. Fludarabine phosphate. Data on file, National Cancer Institute, Bethesda MD, 1982.
9. Hutton, J. J., Von Hoff, D. D., Kuhn J., et al. Phase I clinical investigation of 9-B-D-arabinofuranosyl-2-fluoroadenine 5'-monophosphate (NSC 312887), a new purine antimetabolite Cancer Res. 44: 4183–4186, 1984.
10. Casper, E. S., Mittelman, A. Phase I trial of fludarabine in patients with solid tumors. Proc. Am. Assoc. Cancer Res. 25:203, 1984.
11. Unpublished data on file at the Investigational Drug Branch, Division of Cancer Treatment, National Cancer Institute, Bethesda.
12. Warrell, R. P. Jr., Berman, E. Phase I and II study of fludarabine phosphate in leukemia: Therapeutic efficacy with delayed central nervous system toxicity. J. Clin. Oncol. 4:74–79, 1986.
13. Chun, H. G. Leyland-Jones, BR, Caryk SM, Hoth D. R. Central nervous system toxicity of fludarabine phosphate. Submitted to Cancer Treat. Rep. 1986.
14. Phillips, R. A., Tolmach, L. J. Repair of potentially lethal damage in mammalian cells. Radiat. Res. 29, 414–434, 1966.
15. Hahn, G. M., Little, J. B. Plateau-phase cultures of mammalian cells: an in vitro model for human cancer. Curr. Top. Radiat. Res. Q. 8, 39–83.
16. Iliakis, G. Nusse, M., Bryant, P. Effects of aphidicolin on cell proliferation, repair of potentially lethal damage and repair of DNA strand breaks in Ehrlich ascites tumor cells exposed to x-rays. Int. J. Radiat. Biol. 42, 417–434, 1982.
17. Nakatsugawa, S. potentially lethal damage repair and its implication in cancer treatment. In Modif. Radiosensitivity in Cancer Treatment. Acad. Pres., pp. 221–250, 1984.
18. Weichselbaum, R. J. Nove J., Little, J. B. Radiation response of human tumor cells in vitro. Rad. Biology in Cancer Research. Raven Pres. 345–351, 1980.
19. Weichselbaum, R. J. Little, J. B. The differential response of human tumors to fractionated radiation may be due to a post-radiation repair process. Brit. J. Cancer 46, 532–537, 1982.
20. Iliakis, G. a) Effects of arabinofuranosyladenine on the growth and repair of potentially lethal damaged in Ehrlich ascites tumor cells. Radiat. Res. 83, 537–552, 1980.
21. Nakatsurgawa, S., Sugahara,. T., Kumar, A. Purine necleoside analogues inhibit the repair of radiation-induced potentially lethal damage in mammalian cells in culture. Int. J. radiat. Biol. 41, 343–346, 1982.
22. Hahn, G. M., Van Kersen, I., Silvestrini, B. Inhibition of the recovery from potentially lethal damage by lonidamine. Br. J. Cancer 50, 657–660, 1984.
23. Kim, J. H., Alfieri, A. A., Kim, S. H., Young, C. W. The potentiation of radiation effects on two murine tumors by lonidamine. Cancer Res. in Press, 1986.
24. Kim, J. H., Alfieri, A. A., Kim, S. H., Fuks, Z. Fludarabine phosphate: A new radiosensitizer of meth-A tumor in vivo Cancer letters in Press.
25. Fleiss, J. L. Statistical methods for rates and proportions, 2nd edition, John Wiley & Sons, N.Y., 1981.

What is claimed is:

1. A method of killing sarcoma cells in a patient which comprises:
   1) administering to the patient an effective amount of fludarabine phosphate effective to inhibit the repair of potentially lethal damage to the sarcoma cells; and
   2) exposing the patient to an effective amount of ionizing radiation effective to kill the sarcoma tumor cells in the patient.
2. A method of claim 1, wherein the effective amount of fludarabine phosphate comprises from about 25 to about 375 mg/m$^2$.
3. A method of claim 2, wherein the effective amount of fludarabine phosphate comprises from about 50 to about 250 mg/m$^2$.
4. A method of claim 3, wherein the effective amount of fludarabine phosphate comprises from about 75 to about 200 mg/m$^2$.
5. A method of claim 1, wherein the effective amount of ionizing radiation is from about 6 to about 10 Gray units.
6. A method of claim 5, wherein the effective amount of ionizing radiation is about 8 Gray units.
7. A method of claim 1, wherein the patient is administered fludarabine phosphate at least one hour prior to exposing the treated sarcoma cells to ionizing radiation.

* * * * *